United States Patent
Glen (12)

(10) Patent No.: US 6,239,705 B1
(45) Date of Patent: May 29, 2001

(54) INTRA ORAL ELECTRONIC TRACKING DEVICE

(76) Inventor: Jeffrey Glen, 68 W. Princeton Rd., Bala Cynwyd, PA (US) 19004

( * ) Notice: Subject to any disclaimer, the term of this patent is extended or adjusted under 35 U.S.C. 154(b) by 0 days.

(21) Appl. No.: 09/552,324

(22) Filed: Apr. 19, 2000

(51) Int. Cl.⁷ ....................................................... H04Q 1/30
(52) U.S. Cl. .................................... 340/573.1; 340/572.8; 340/573.4
(58) Field of Search ............................ 340/573.1, 573.4, 340/572.8; 433/8, 37, 38, 80

(56) References Cited

U.S. PATENT DOCUMENTS

| | | |
|---|---|---|
| 3,034,356 | 5/1962 | Bieganski et al. . |
| 3,297,021 * | 1/1967 | Davis et al. ............................... 128/2 |
| 3,852,713 | 12/1974 | Roberts et al. . |
| 4,629,424 * | 12/1986 | Lauks et al. ............................... 433/6 |
| 4,706,689 * | 11/1987 | Man . |
| 5,383,915 * | 1/1995 | Adams . |
| 5,476,488 * | 12/1995 | Morgan et al. ......................... 607/30 |
| 5,629,678 * | 5/1997 | Gargano et al. . |
| 5,760,692 * | 6/1998 | Block .................................... 340/573 |
| 5,954,673 * | 9/1999 | Staehlin et al. ....................... 600/590 |

OTHER PUBLICATIONS

Personal Satellite Tracking Applications.
Protect your child, via satellite.

* cited by examiner

*Primary Examiner*—Jeffery Hofsass
*Assistant Examiner*—Son Tang
(74) *Attorney, Agent, or Firm*—McNees, Wallace & Nurick; Mitchell A. Smolow; Carmen Santa Maria

(57) ABSTRACT

An improved stealthy, non-surgical, biocompatable electronic tracking device is provided in which a housing is placed intraorally. The housing contains microcircuitry. The microcircuitry comprises a receiver, a passive mode to active mode activator, a signal decoder for determining positional fix, a transmitter, an antenna, and a power supply. Optionally, an amplifier may be utilized to boost signal strength. The power supply energizes the receiver. Upon receiving a coded activating signal, the positional fix signal decoder is energized, determining a positional fix. The transmitter subsequently transmits through the antenna a position locating signal to be received by a remote locator. In another embodiment of the present invention, the microcircuitry comprises a receiver, a passive mode to active mode activator, a transmitter, an antenna and a power supply. Optionally, an amplifier may be utilized to boost signal strength. The power supply energizes the receiver. Upon receiving a coded activating signal, the transmitter is energized. The transmitter subsequently transmits through the antenna a homing signal to be received by a remote locator.

20 Claims, 4 Drawing Sheets

FULL DENTURE

INTRA ORAL ELECTRONIC TRACKING DEVICE

FIELD OF THE INVENTION

The present invention relates generally to an electronic tracking and locating system, and more specifically, to an improved system whereby a transducer is placed intraorally.

BACKGROUND OF THE INVENTION

Numerous electronic devices have been introduced to track and locate mobile assets, such as for example, trucks, rail cars, and shipping containers. Hundreds of thousands of these assets have been equipped with tracking and locating transducers. The most sophisticated systems permit location of an asset to within a few feet.

More recently, systems to track and locate people have been developed. These tracking and locating devices are useful in managing persons who may be incapable or unable to seek assistance, such as for example, people with Alzheimer's disease, prisoners, children, and military personnel. Additional systems have been proposed to track pets and other animals.

Transmitters and transceivers utilized in locating and tracking humans have been worn as bracelets, sewn into clothing, placed in backpacks, implanted behind the ear of a human, and implanted, generally, under the skin.

One such system utilizes global positioning satellite technology to track and locate inanimate objects, animals, and humans. In one form, a bracelet containing a receiver is worn by a child. Utilizing the known location of three orbiting satellites and the time it takes for a signal to travel between the transducer and each of the three satellites, a three-dimensional position of the transducer is able to be calculated.

In addition to a receiver being worn as a bracelet, systems have been used employing a self-powered self-maintained transceiver, small enough to be implanted under the skin, for locating, tracking and recovering persons in distress such as for example, kidnap victims, people encountering adverse circumstances while in the wilderness, victims of heart attacks, and the like.

Other systems have been used which remain passive until remotely activated. For example, one recovery system employs a transceiver hidden within a motor vehicle and a network of fixed and mobile ground transmitters and receivers to facilitate tracking and recovery of stolen vehicles. The unit is continuously operated as a receiver until it is remotely activated. Once activated, it transmits a radio beacon facilitating tracking and recovery. Ground based fixed and mobile receiver units utilizing field strength measurements and directional receivers then are able to locate the transmitter.

Location and recovery systems have also been developed using timing and triangulation methods, such as that used by the Emergency Position Indicating Radio Beacons (EPIRB). Using the global positioning satellite system, once the user activates a transmitter, the associated satellite network is capable of locating a transmitting EPIRB anywhere on the face of the globe.

Receivers and transceivers worn as jewelry or sewn into clothing are easily found and removed, limiting their usefulness for military, intelligence and personal protection applications. Receivers and transceivers implantable under the skin require an invasive surgical procedure to implant these devices, and additional invasive surgical procedures to repair or remove the device. In addition, surgically implanted devices are susceptible to infection and may be rejected by the body's autoimmune defense system. For these reasons, implanted devices have a low acceptance rate among potential users, particularly, children.

What is needed is a stealthy, non-surgical, biocompatible way to attach a transducer to a living organism such as an animal or human being which can be utilized for tracking and locating a human being or animal.

SUMMARY OF THE INVENTION

In accordance with an aspect of the present invention, an improved stealthy, non-surgical, biocompatable electronic tracking device is provided in which a housing is placed intraorally. The housing contains microcircuitry. The microcircuitry comprises a receiver, a passive mode to active mode activator, a signal decoder for determining positional fix, a transmitter, an antenna, and a power supply. Optionally, an amplifier may be utilized to boost signal strength.

The power supply energizes the receiver. The receiver is in a passive mode until it is activated, to conserve power. Upon receiving a coded activating signal, the positional fix signal decoder is energized, determining a positional fix. The transmitter subsequently transmits through the antenna a position locating signal to be received by a remote locator.

In another embodiment of the present invention, the microcircuitry comprises a receiver, a passive mode to active mode activator, a transmitter, an antenna and a power supply. Optionally, an amplifier may be utilized to boost signal strength. The power supply energizes the receiver. Upon receiving a coded activating signal, the transmitter is energized. The transmitter subsequently transmits through the antenna a homing signal to be received by a remote locator.

In still another embodiment of the present invention, the power supply is replaced by a power storage device. Power is supplied to the storage device by establishing an intraoral galvanic reaction utilizing saliva and differing metals placed within the oral cavity, or alternatively, by collecting and storing RF energy.

The transmitter may be activated by the user or activation may be triggered by an external event, such as for example, a received coded RF signal or coded electromagnetic signal from, for example, a global positioning satellite ("GPS") signal. The tracking device is preferably capable of being programmed to remain in a dormant or passive mode until receiving an activating signal.

The tracking device can be affixed to the external surface of a tooth or teeth through the use of dental adhesives, bonding agents and/or ligation, or it may be incorporated completely within a dental restoration, endodontically prepared root canal system, a prosthetic tooth or denture.

One advantage of the present invention is that placement of the tracking device intraorally does not require an invasive procedure. In this manner, the device may be stealthy, yet still maintain non-surgical accessibility for maintenance and repair.

Another advantage of the present invention is the ease of removal when the device is meant to be utilized only for a short period of time.

Still another advantage of the present invention is the ability to utilize the galvanic potential of the oral cavity to power the device, eliminating or reducing the need for a separate power supply.

When an internal power supply is utilized, the intra oral location makes for easy accessibility to recharge the power supply without removing the device.

Still another advantage of the present invention is the ability to easily and regularly confirm the operability of the device during routine dental recall visits.

Another advantage of the present invention is the ability to service, replace or remove the locating unit on a regular basis during routine dental visits.

Another advantage of the present invention is the ability of a remote operator to activate and deactivate the transmitting feature of the locating unit, as necessitated by security requirements.

Still another advantage of the present invention is the relative ease of insertion intraorally, with excellent stealth capabilities.

Yet another advantage of the present invention is the ability for a military commander or police commander to know where their troops are at any given moment.

Other features and advantages of the present invention will be apparent from the following more detailed description of the preferred embodiment, taken in conjunction with the accompanying figures which illustrate, by way of example, the principles of the invention.

DETAILED DESCRIPTION OF THE PREFERRED EMBODIMENTS

Figure 1:
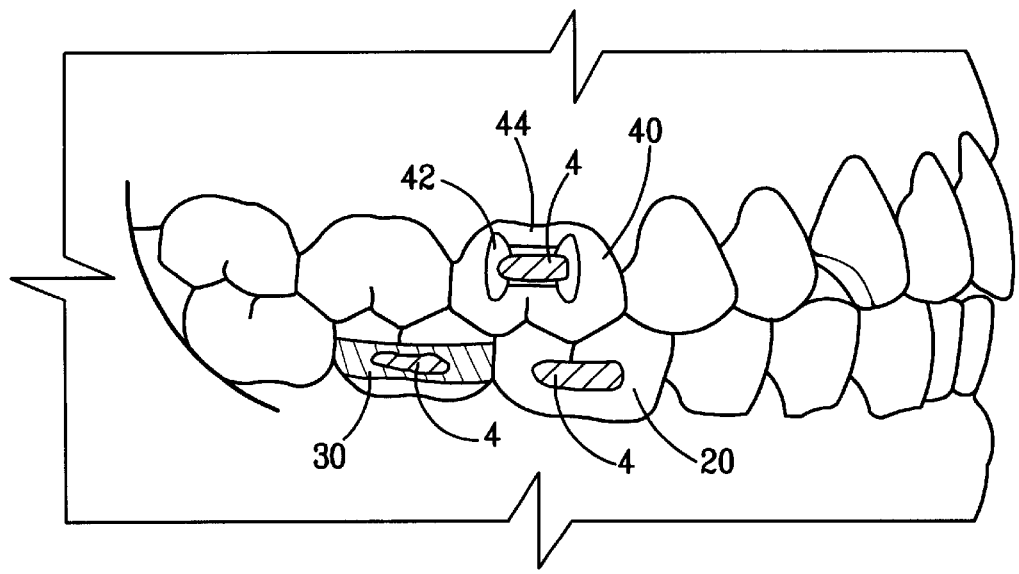
FIG. 1 is a frontal view of three possible tooth attachment methods of the present invention.

Referring now to the Figures, where like parts have the same numbers, in accordance with a preferred embodiment of the invention, an improved electronic tracking device is provided for use in both humans and animals. The device comprises a housing 4 affixed intraorally. The housing 4 contains microcircuitry 6. The microcircuitry 6 comprises a receiver 8, a passive mode to active mode activator 10, a signal decoder 12 for determining positional fix, a transmitter 14 for transmitting an electromagnetic (EM) signal, an antenna 16 and a power supply or source 18.

While optional, it is desirable that the housing 4 be rigid or a semi-rigid encasement to enhance rigidity and inhibit straining of the device. The housing 4 is manufactured from an oral biocompatible material such as for example, porcelain or other orally compatible ceramic, gold, chrome-cobalt alloy or other orally biocompatible alloy, acrylic, stainless steel, or titanium. When placed external to the tooth 20, the shape of the housing 4 should be self-cleansing, for example, smooth and without sharp contours, for example, in the shape of a half moon or oval or round, so as not to trap plaque and food particles thereby minimizing the risk for dental decay and periodontal disease, and so as to minimize abrasion of oral soft tissues, for example the tongue and oral mucuso of the cheek.

The housing 4 should be retentive so as not to dislodge and be swallowed.

As shown in FIG. 1, when placed external to the tooth 20 (or teeth, if required by the housing dimension), the housing may be adhered directly to the tooth 20 utilizing known dental bonding techniques. To enhance bond strength, the bonding surface of the housing 4 may be a rough surface, such as for example, etched or meshed to increase mechanical bond retention. While a universal shape may be utilized, to further enhance bond strength, optionally, the housing 4 should be contoured to a mirror image of the tooth 20 surface to which it will be bonded. This may be accomplished, for example by taking an impression of the tooth and custom fabricating the housing 4 in a laboratory procedure.

Alternatively, the housing 4 may be attached to an orthodontic band 30, stainless steel crown or other type of crown 40 which is cemented to the tooth. The housing 4 may be positioned buccally or lingually. A lingual placement provides for better cosmetics and increased stealthiness. Whether placed buccally or lingually, the housing 4 should be placed in an occlusal-gingival position so as to minimize any local inflammatory response.

Figure 2:
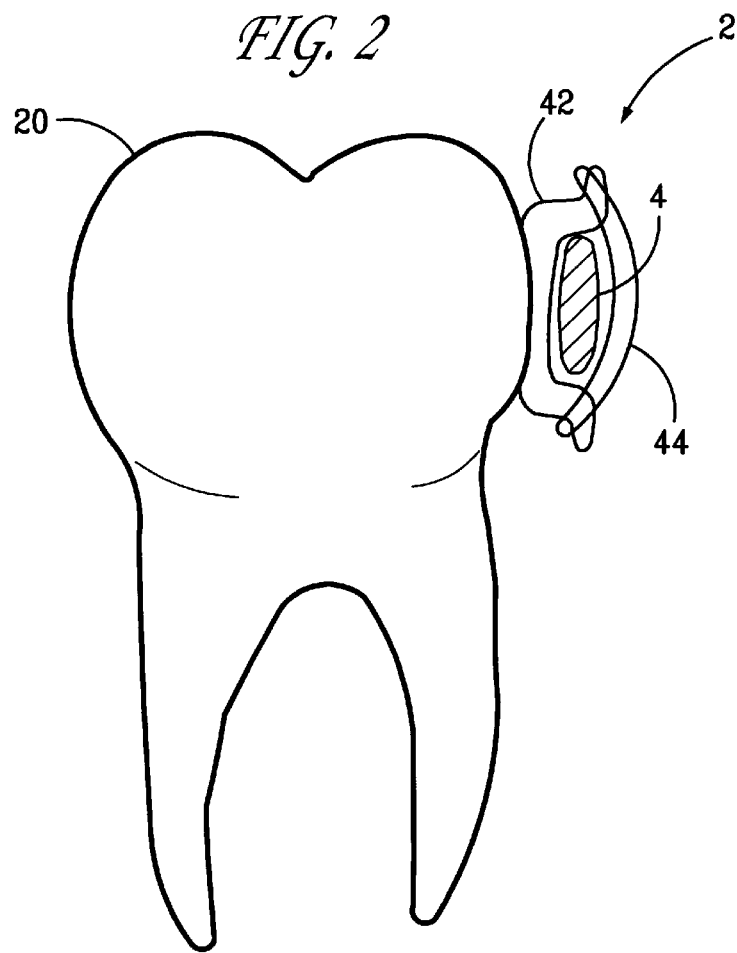
FIG. 2 is a profile view of the housing contained within a receiving receptacle.

When attached to a crown 40 for example, a stainless steel crown, a porcelain crown, a porcelain fused to metal crown, an acrylic crown, or a porcelain or acrylic veneer crown, the crown 40 may be fabricated in the laboratory with a receiving receptacle 42 to receive the housing. Alternatively, the receiving receptacle 42 may be welded or spot welded to the crown 40. As shown in FIG. 2, the housing 4 may then be inserted into the receiving receptacle 42 and held in place within the receiving receptacle 42 by for example, ligating with stainless steel or brass ligature wire 44, or it may be held in place within the receiving receptacle 42 utilizing orthodontic elastomerics, or it may be held in place within the receiving receptacle with a rigidly flexible retaining arm (not shown). In this manner, the housing 4 may be easily removed for maintenance, repair, or replacement.

The receiving receptacle 42 may be attached for example, by welding or spot welding to an orthodontic band 30. The orthodontic band 30 may then be cemented to a tooth 20, the housing 4 inserted into the orthodontic band 30 receiving receptacle 42, and held in place within the receiving receptacle 42 by any of the retaining methods described above.

Alternatively, a receiving receptacle 42 may be attached for example, by welding or spot welding to matrix material such as for example, stainless steel matrix material (not shown). The matrix material is then fit to the tooth 20, crimped, and spot welded, forming a custom band 30. After cementation of the band 34 to the tooth 20, the housing 4 is then retained within the matrix material receiving receptacle 42 in a manner as described above.

Still another alternative is to bond a receiving receptacle 42 directly to the tooth 20 using the methods described above or by other bonding methods well known in the art. The receiving receptacle 42 bonding surface should optionally be rough as for example, by etching or use of a mesh or micro projections, to promote bond adherence. After bonding to the tooth 20, the housing 4 is attached to the receiving receptacle 42 as described above.

Although effective on any tooth, the optimal location for an externally placed housing 4 or combination housing 4/receiving receptacle 42 is the mandibular second primary molar when placed in the primary dentition, or the first or second mandibular permanent molar when placed in the permanent dentition. These teeth provide the broadest contours to accept the device, provide an unobtrusive location, will not interfere with eating or other functions in the mouth and are easy to keep clean.

Figure 3:
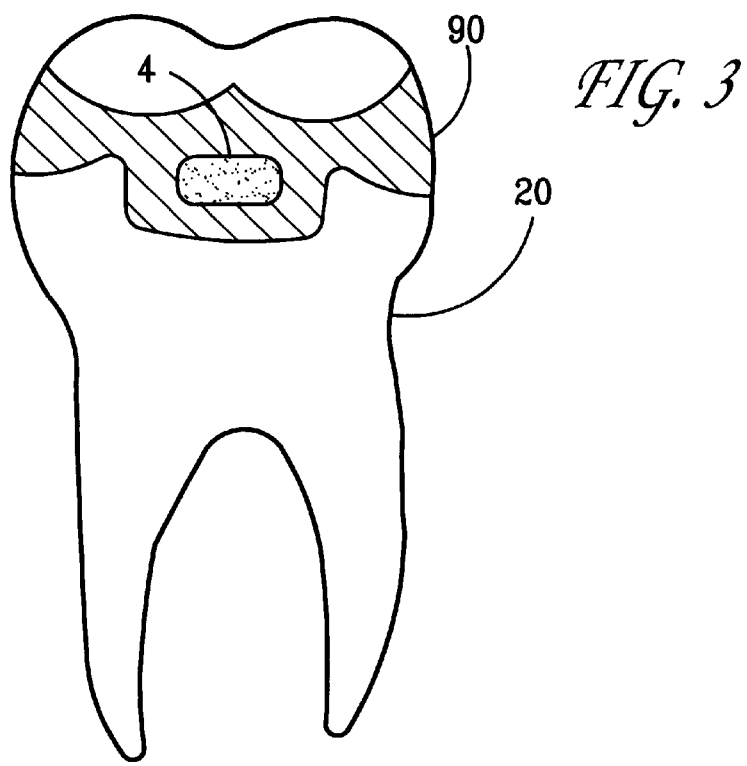
FIG. 3 is a view of the housing placed within a dental restoration.
Figure 4:
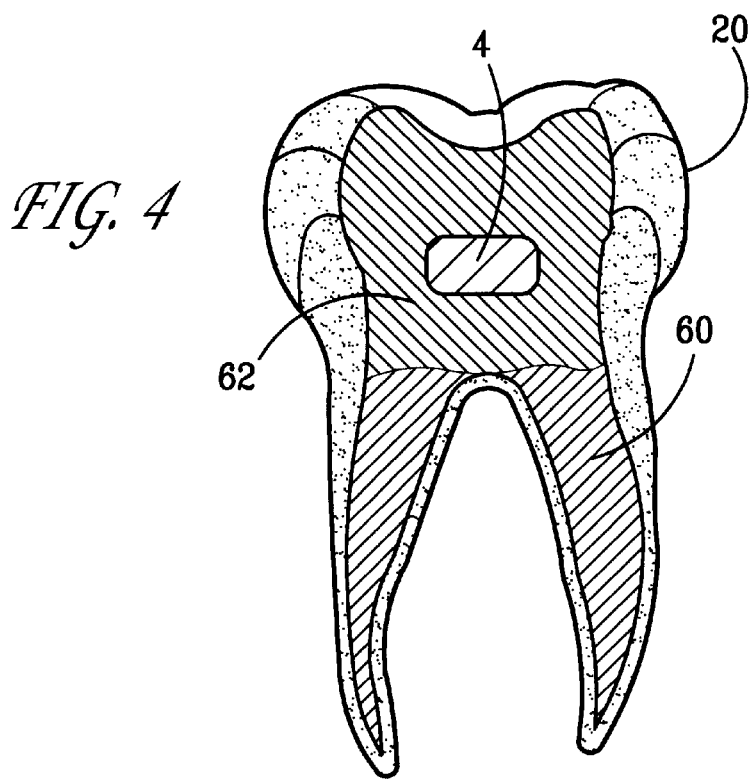
FIG. 4 is a view of the housing placed within an endodontically treated tooth.
Figure 5:
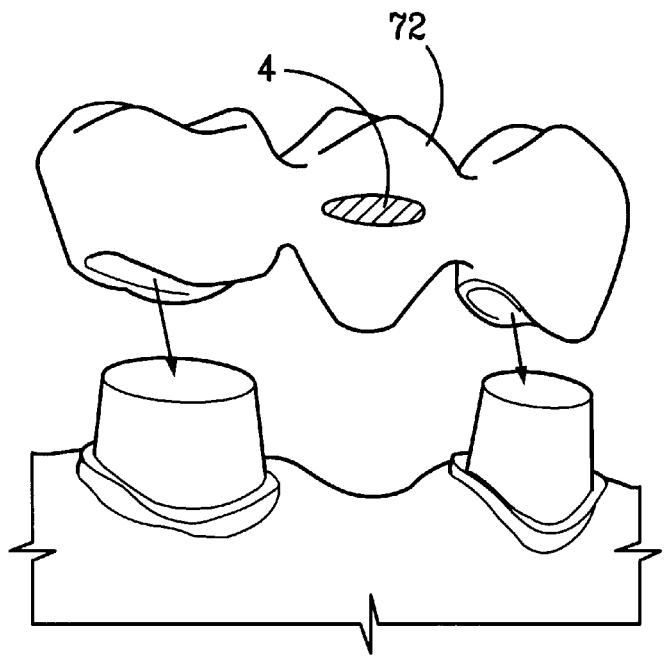
FIG. 5 is a view of the housing placed within a fixed prosthesis.

As shown in FIGS. 3–5, the housing 4 may be incorporated into any number of restorations 90 such as for example, crowns, onlays, inlays, amalgam restorations, composite restorations, and prosthetic teeth. When preparing a tooth 20 to receive a crown, sufficient tooth structure should be removed to permit the incorporation of the housing within the crown 40 itself. It should be appreciated that when the housing 4 is incorporated as part of a crown design, access to the housing 4 cannot be effectuated without removal of the crown 40, however, accessibility to recharge a power supply 18 is still maintained.

For example, a recharging device, such as a toothbrush shaped wand can be inserted into the mouth to contact the crown 40 at a predetermined recharging point which is electrically connected to a rechargeable power supply, for example, a rechargeable battery or capacitor, to transfer a charge to the rechargeable power supply.

Likewise, when a tooth is to be treated endodontically (FIG. 4), the housing 4 may be incorporated within the root canal obturation system 60, or as part of a core buildup 62. In the primary dentition, a prophylactic pulpotomy may be performed to provide adequate space to incorporate the housing 4 within a stainless steel crown.

As advances in microcircuitry and microbattery techniques permit smaller and smaller housings, the housings 4 may be placed under or within dental restorations 90, (FIG. 3) for example, amalgam or composite restorations. Conservative prophylactic restorations for example, Class I or Facial preparations may be prepared to receive the housing 4.

Figure 6:
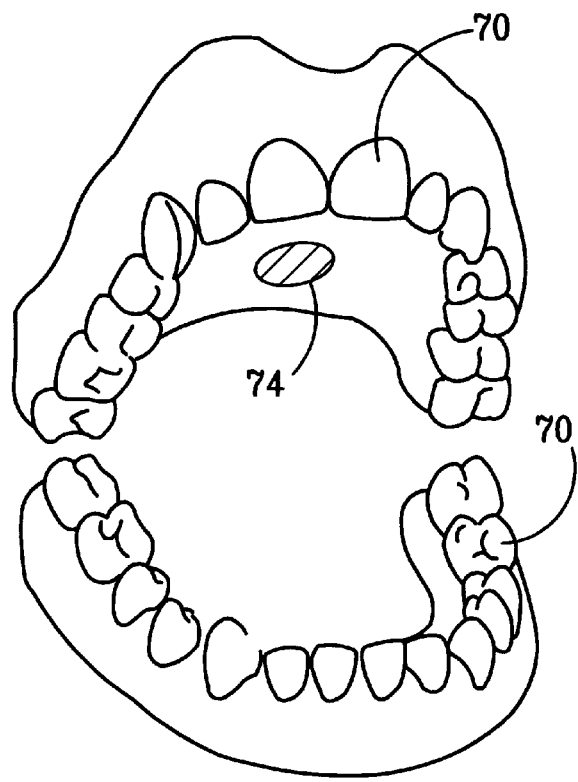
FIG. 6 is a view of the housing placed within a removable prosthesis.

Referring to FIGS. 5 and 6, the housing 4 may be incorporated into a prosthetic tooth 70, either fixed or removable, or incorporated into the prosthesis itself 74. For example, the housing 4 may be contained within the pontic 72 of a fixed bridge, for example, a cemented bridge or bonded bridge; or it may be contained within a prosthetic tooth 70 of a removable denture, for example a full denture, a partial denture, a precision attachment appliance or an overdenture. An advantage of placing the housing 4 within a removable denture is the ease of repair and replacement of the unit, as well as the ability to place a housing 4 or antenna 16 of larger size.

The housing 4 optionally may be incorporated into a removable retainer for example, an orthodontic retainer, or may be incorporated into a fixed or removable splint, for example a periodontal splint.

Figure 7:
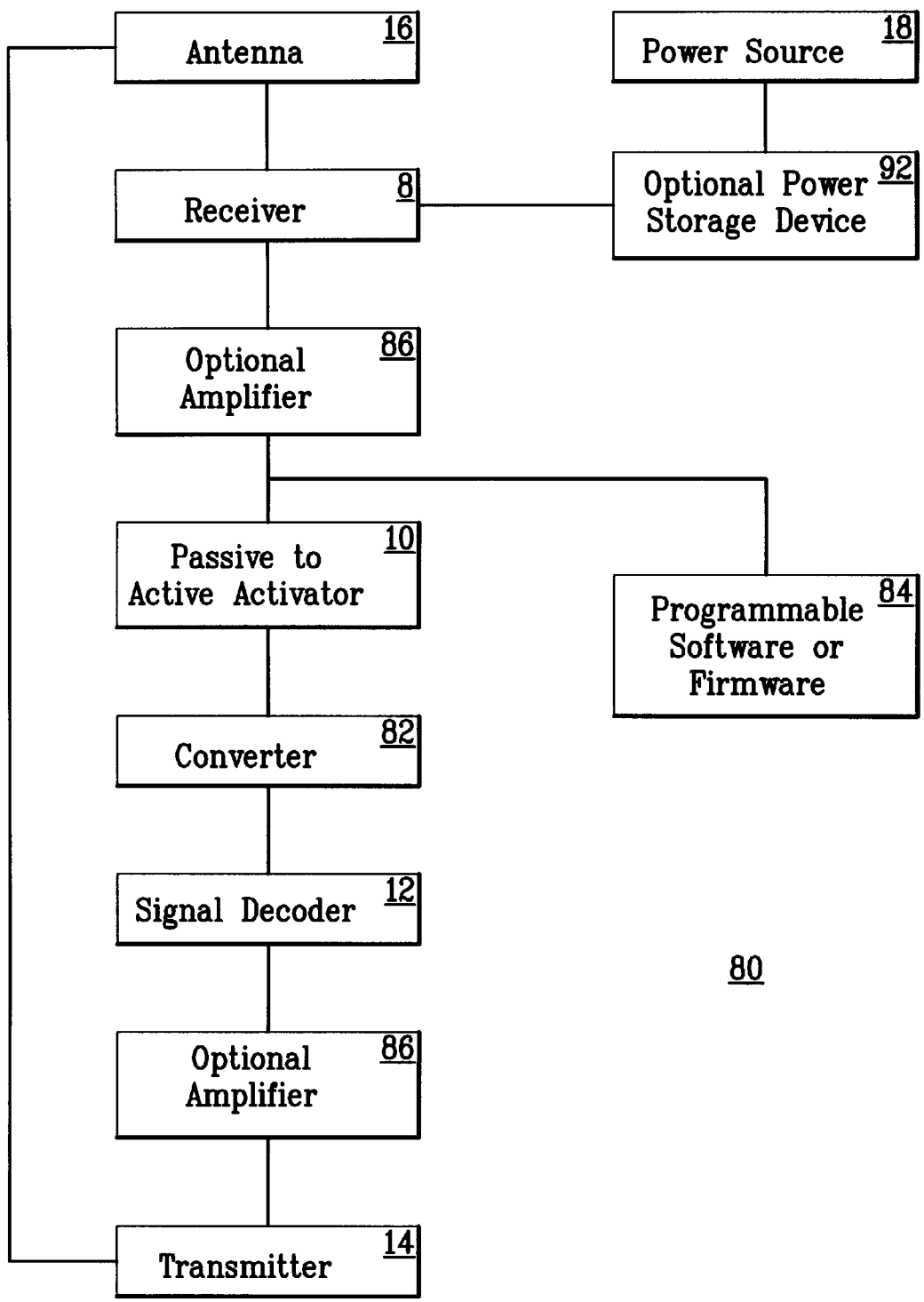
FIG. 7 is a block diagram of the housing components.

Referring now to the block diagram of FIG. 7, the housing 4 contains a suitable material to hold the various components, for example, a board, a wafer, or other substrate material 80 suitable for circuits. The integrated circuit optionally, but preferably includes one or more converters 82 for coding internal or external signals. Preferably, the converters 82 are digital converters for coding internal and external digital signals. The integrated circuit further includes a receiver 8 calibrated to receive at least one external signal, passive mode to active mode activator 10, signal decoder 12 for determining positional fix, transmitter 14 for transmitting an electromagnetic signal, antenna 16, programmable software 84 or firmware, and power supply 18 for use with the invention. The components are commercially available and/or can be fabricated. Optionally, shielding (not shown) may be provided to protect sensitive anatomical areas from transmission energy and/or one or more amplifiers 86 may be utilized to boost signal strength.

In use, the present invention operates as follows. After examining the patient, the dentist selects the optimal location for placement of the housing 4, preferably the buccal surface of the mandibular second primary molar when placed in the primary dentition, or the mandibular first or second permanent molar when placed in the permanent dentition. If stealthiness is the primary consideration, i.e., as in military use, intelligence use or for personal protection, an endodontically treated tooth is selected, or alternatively, an appropriate tooth to be restored with a crown may be selected.

If external placement is indicated, to achieve maximum retention, an impression of the tooth 20 is taken utilizing standard impression techniques. A working model of the tooth 20 is poured from the impression, and a contoured housing 4 is fabricated in a laboratory.

Alternatively, a contoured receiving receptacle 42 is fabricated in the laboratory. The advantage of custom contouring the receiving receptacle 42 rather than the housing 4 is that the housing 4 and its components, by far the most costly to produce, may be mass produced to a standard size able to be placed into any custom contoured receiving receptacle 42.

A direct chairside technique using prefabricated materials is also acceptable, although laboratory fabrication of a working model provides better contouring of the bonding surface and thus, increased bond strength.

If an orthodontic band 30 is clinically indicated, a pre-sized orthodontic band may be utilized, however, preferably a custom fit orthodontic band or matrix band is laboratory fabricated to the working model, after which a receiving receptacle 42 is permanently attached for example, welded or spot welded to the orthodontic or matrix band. Less preferable, but still acceptable, the housing 4 itself may be permanently attached to the orthodontic or matrix band, or ligated to a standard orthodontic bracket.

The housing 4 (custom contoured or preformed), receiving receptacle 42 (custom contoured or preformed), or orthodontic 30 or matrix band, as clinically indicated, is then bonded or cemented to the tooth 20 in a location so as to cause minimal irritation and localized inflammation. Where a receiving receptacle 42 has been utilized, the housing 4 is then placed in the receiving receptacle 42 and ligated in place using for example, stainless steel or brass ligature wire 44 or elastomeric thread or held in place with elastomeric bands or a rigidly flexible retaining arm.

The housing 4 may be mass produced, yet still be customizable by the dentist or laboratory by for example, adding mesh or other retentive material to the housing 4 to increase the retentive area.

If an endodontically treated tooth is selected to contain the housing, a post and core 62 is fabricated (either laboratory fabricated or chairside) incorporating a receiving area for the housing 4. The housing 4 is then placed into the receiving area and a crown 40 is fabricated to cover the housing 4, post, and core 62 combination utilizing standard prosthetic techniques.

The housing 4 and electronic components (hereinafter called the "locating unit 2") is in passive mode. While in passive mode, to reduce power consumption, only the receiver 8 is energized. When it is desirable for a person's location to be determined, for example when they have not maintained contact for a predetermined period of time, a coded signal is transmitted, for example through a satellite transmitter. Upon receiving this coded signal, the passive to active mode activator 10 switches the locating unit 2 from the passive mode to active mode, or from an "off" position to an "on" position. The use of a coded signal specific to that locating unit 2 allows for selectivity as to which locating unit 2 is to be activated.

Alternatively, the coded signal may be activated by the user himself, for example by using a handheld transmitter or by an activation point on the housing 4 itself. When utilized for personal protection or by the military or intelligence agencies, the user activated coded signal transmitter (not shown) may be hidden or disguised. After the initial coded signal has been sent and the locating unit 2 switched to active mode, the coded signal transmitter (not shown) may be discarded.

Once in active mode, a signal decoder 12 for determining positional fix utilizing for example, global positioning satellite technology determines an exact three-dimensional location of the locating unit. This information is then transmitted via the transmitter 14 and antenna 16 to a remotely located receiver (not shown). An operator at the remotely located receiver is then able to determine the exact three-dimensional position of the locating unit 2 and hence, the person.

When used in military, intelligence, or other sensitive operations, the coded activating signal as well as the transmitted location signal are optionally encrypted so as not to alert an adversary of the location of the locating unit. The programmable software or firmware 84 is programmed to allow a received second coded and encrypted signal to return the locating unit to passive mode, thus preventing the locating unit from transmitting, and thereby reducing the opportunity for an adversary to get a fix on the locating unit 2. Alternatively, in all embodiments, the locating unit 2 may be programmed to return to passive made after a predetermined period of time, thus conserving power and also reducing the risk of discovery by an adversary.

While in the preferred embodiment, the power supply 18 for example, a microbattery is contained within the housing, utilizing galvanic principles, a power storage device 92 could be substituted for the power supply contained within the housing. It is well known that when differing metals are present in the mouth, for example, a filling in a tooth and tinfoil, the metals become electrically charged. Oral fluids such as salvia act as an electrical conductor, allowing electrons to flow between the two metals through the salvia.

Utilizing these principles, this electric charge may be collected and stored in the voltage storage device and utilized to power the locating unit. Optionally, a combination microbattery 18 power supply and power storage device 92 may be utilized to increase the life of the battery 18.

Alternatively, energy to be stored in the voltage storage device may be transferred via a coded RF beam, optionally multiplexed with the coded activation/deactivation signals.

In a different embodiment of the present invention, the signal decoder for determining positional fix is omitted.

Upon switching to active mode after receiving a coded signal, the transmitter 14 begins to transmit a signal beacon at regular intervals, for example about once every ten minutes, ideally about once per minute. The signal is compatible with cellular phone signals used to alert mobile telephone companies of the cell location of mobile phones. With this signal, and with the cooperation of the cellular phone companies, the current mobile phone cell location of the locating unit can be detected.

Existing mobile phone technology allows the signal to be located within a small area of a cell. A mobile direction finding and locating device can then be brought to this pre-determined small cell area, and utilizing known locating and direction finding technologies, the signal homing beacon being transmitted by the locating unit, and hence, the person can be found.

In yet another embodiment, the transmitting signal beacon is received by orbiting satellites. Utilizing GPS technology, the satellites are able to determine the exact location of the locating unit and relay that location to a remote operator, or alternatively, the orbiting satellites relay the raw data to a remote location for determination of the locating unit's position.

Although the present invention has been described in connection with specific examples and embodiments, those skilled in the art will recognize that the present invention is capable of other variations and modifications within its scope. For example, the housing or the receiving receptacle may be removably attached using hook and loop technology.

These examples and embodiments are intended as typical of, rather than in any way limiting on, the scope of the present invention as presented in the appended claims.

What I claim is:

1. An electronic tracking device comprising:
an intraorally, nonsurgically placed housing comprising a power supply in communication with a receiver calibrated to receive at least one coded external signal and a transmitter to transmit a coded electromagnetic signal.

2. The electronic tracking device of claim 1 further comprising a signal decoder in communication with the transmitter for determining a positional fix.

3. The electronic tracking device of claim 2 wherein the coded transmitted signal is the positional fix determined by the signal decoder.

4. The electronic tracking device of claim 1 wherein the receiver communicates with a passive mode to active mode activator which upon receiving a coded activating signal energizes the transmitter to transmit a coded signal through an antenna to be received by a remotely located receiver.

5. The electronic tracking device of claim 1 wherein the at least one coded external signal is a coded activating signal and a coded deactivating signal.

6. The electronic tracking device of claim 1 wherein the at least one coded external signal is a coded activating signal, a coded deactivating signal, and a coded power supplying signal.

7. The electronic tracking device of claim 1 wherein the at least one coded external signal is sent by at least one orbiting satellite.

8. The electronic tracking device of claim 1 further comprising programmable software or firmware in communication with the receiver.

9. The electronic tracking device of claim 1 wherein the housing is affixed to a tooth surface.

10. The electronic tracking device of claim 9 wherein the housing is removably held within a receiving receptacle which is affixed to the tooth surface.

11. The electronic tracking device of claim 1 wherein the housing is placed within one of the group consisting of a tooth, fixed prosthesis, and removable prosthesis.

12. The electronic tracking device of claim 1 wherein the power supply is a battery.

13. The electronic tracking device of claim 1 wherein the power supply is a power storage device, the power storage device receiving its power from an intraoral galvanic reaction.

14. The electronic tracking device of claim 1 wherein the power supply is a power storage device, the power storage device receiving its power from a received coded RF beam.

15. The electronic tracking device of claim 1 wherein the coded transmitted signal is a signal homing beacon.

16. A method for locating a human or animal comprising the steps of:
   a) nonsurgically placing an intraoral housing comprising a power supply in communication with a receiver calibrated to receive at least one external coded signal and a transmitter to transmit a coded electromagnetic signal;
   b) receiving a coded activating signal, the signal initiating a determination of a positional fix; and
   c) transmitting the positional fix to a remotely located receiver.

17. The method of claim 16 further comprising the step of receiving a coded deactivation signal after the remotely located receiver has received the positional fix.

18. The method of claim 17 wherein the coded signals are encrypted.

19. A method for locating a human or animal comprising the steps of:
   a) nonsurgically placing an intraoral housing comprising a power supply in communication with a receiver calibrated to receive at least one external coded signal and a transmitter to transmit a coded electromagnetic signal;
   b) receiving a coded activating signal;
   c) transmitting, upon activation, a signal homing beacon to a remotely located receiver; and
   d) homing in on the transmitted signal beacon.

20. The method of claim 19 wherein the transmitted signal beacon is received by a receiver selected from the group consisting of a cell phone tower and a plurality of orbiting satellites.

\* \* \* \* \*